United States Patent
Yu et al.

(10) Patent No.: US 10,980,854 B2
(45) Date of Patent: *Apr. 20, 2021

(54) NUTRITION BLEND FOR HEALTH BENEFITS IN ANIMALS

(71) Applicant: Societe des Produits Nestle S.A., Vevey (CH)

(72) Inventors: Ping Yu, St. Louis, MO (US); Yuanlong Pan, Chesterfield, MO (US)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 386 days.

This patent is subject to a terminal disclaimer.

(21) Appl. No.: 16/179,341

(22) Filed: Nov. 2, 2018

(65) Prior Publication Data

US 2019/0134132 A1    May 9, 2019

Related U.S. Application Data

(60) Provisional application No. 62/583,818, filed on Nov. 9, 2017.

(51) Int. Cl.

| | | |
|---|---|---|
| A61K 36/00 | (2006.01) | |
| A61K 36/52 | (2006.01) | |
| A61P 3/00 | (2006.01) | |
| A61K 36/07 | (2006.01) | |
| A61K 31/353 | (2006.01) | |
| A61K 36/9066 | (2006.01) | |
| A61K 31/01 | (2006.01) | |
| A23K 50/40 | (2016.01) | |
| A61K 31/201 | (2006.01) | |
| A61K 31/202 | (2006.01) | |
| A23K 10/30 | (2016.01) | |
| A23K 20/121 | (2016.01) | |
| A23K 20/105 | (2016.01) | |
| A23K 20/158 | (2016.01) | |
| A61K 31/145 | (2006.01) | |
| A61P 3/04 | (2006.01) | |
| A61K 36/53 | (2006.01) | |

(52) U.S. Cl.
CPC ............. *A61K 36/52* (2013.01); *A23K 10/30* (2016.05); *A23K 20/105* (2016.05); *A23K 20/121* (2016.05); *A23K 20/158* (2016.05); *A23K 50/40* (2016.05); *A61K 31/01* (2013.01); *A61K 31/145* (2013.01); *A61K 31/201* (2013.01); *A61K 31/202* (2013.01); *A61K 31/353* (2013.01); *A61K 36/00* (2013.01); *A61K 36/07* (2013.01); *A61K 36/53* (2013.01); *A61K 36/9066* (2013.01); *A61P 3/00* (2018.01); *A61P 3/04* (2018.01)

(58) Field of Classification Search
CPC .................................................... A61K 36/00
USPC ........................................................ 424/725
See application file for complete search history.

(56) References Cited

FOREIGN PATENT DOCUMENTS

| | | | |
|---|---|---|---|
| CN | 102113667 A | * | 7/2011 |
| WO | 201103045 A1 | | 1/2011 |

OTHER PUBLICATIONS

Packer, Rowena M.A, et al., "Effects of a ketogenic diet on ADHD-like behavior in dogs with idiopathic epilepsy" Epilepsy & Behavior, 2016, 55 62-68 US and UK.

Ngo, S.T. et al, "High Caloric Diets in Amyotrophic Lateral Sclerosis," Chapter 36, 2015 XP0009510709 pp. 355-361, Australia.

International Search Report & Written Opinion, Transmittal, PCT/IB2018/058639 dated Feb. 21, 2019.

* cited by examiner

*Primary Examiner* — Michael V Meller

(57) ABSTRACT

A method of minimizing fat accumulation in a growing animal without limiting caloric intake or preventing or treating obesity in an animal, the method comprising orally administering a ketogenic diet and a nutrient blend to the animal. The nutrient blend can include at least four nutrients selected from the group consisting of walnut, maitake mushroom extract, EGCG, turmeric root powder, lycopene, taurine, EPA, and DHA to the animal.

13 Claims, No Drawings

NUTRITION BLEND FOR HEALTH BENEFITS IN ANIMALS

CROSS REFERENCE TO RELATED APPLICATIONS

This application claims priority to U.S. Provisional Application No. 62/583,818 filed Nov. 9, 2017, the disclosure of which is incorporated herein by this reference.

BACKGROUND

The rates of obesity and overweight have increased drastically over recent decades, and the prevalence of obesity and overweight tends to increase with age. Obesity and overweight are correlated with numerous pathologies, including sleep apnea, metabolic syndrome, cardiovascular disease, diabetes, cancer, and general deterioration of patients' feelings of wellness. Overweight and obese patients can also suffer from multiple symptoms aside from the aforementioned pathologies, including fatigue, drowsiness, lack of motivation, anhedonia, and depression. Inflammatory diseases, such as arthritis, have been shown to be exacerbated by excess weight, which may be an effect of increased adipocyte proliferation and the concomitant increased activity of adipose tissue specific cytokines known as adipokines.

As such, ongoing research and study continue in efforts to find alternative solutions for fat accumulation and obesity

SUMMARY

The present disclosure relates generally to ketogenic diets and nutrient blends. More specifically, the present disclosure relates to methods and compositions directed to ketogenic diets and nutrient blends for minimizing fat accumulation in a growing animal without limiting caloric intake or preventing or treating obesity in an animal.

Accordingly, in a general embodiment, a method of minimizing fat accumulation in a growing animal without limiting caloric intake or preventing or treating obesity in an animal can comprise orally administering a ketogenic diet and a nutrient blend to the animal. The nutrient blend can include at least four nutrients selected from the group consisting of walnut, maitake mushroom extract, EGCG, turmeric root powder, lycopene, taurine, EPA, and DHA to the animal.

Additional features and advantages are described herein and will be apparent from, the following Detailed Description.

DETAILED DESCRIPTION

Definitions

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the singular forms "a," "an" and "the" include plural referents unless the context clearly dictates otherwise. Thus, for example, reference to "an ingredient" or "the ingredient" includes two or more ingredients. The term "and/or" used in the context of "X and/or Y" should be interpreted as "X," or "Y," or "X and Y." Where used herein, the term "example," particularly when followed by a listing of terms, is merely exemplary and illustrative, and should not be deemed to be exclusive or comprehensive.

As used herein, "about" is understood to refer to numbers in a range of numerals, for example the range of −10% to +10% of the referenced number, preferably within −5% to +5% of the referenced number, more preferably within −1% to +1% of the referenced number, most preferably within −0.1% to +0.1% of the referenced number. A range that is "between" two values includes those two values. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the total weight of the composition unless expressed otherwise. When reference is made to the pH, values correspond to pH measured at 25° C. with standard equipment.

The terms "food," "food product" and "food composition" mean a product or composition that is intended for ingestion by an animal and provides at least one nutrient to the animal. The term "pet food" means any food composition intended to be consumed by a companion animal.

The term "animal" refers to any animal that could benefit from one or more of the methods or compositions of the present invention including human, avian, bovine, canine, equine, feline, hircine, lupine, murine, ovine, and porcine animal. In one embodiment, the animal can be a companion animal.

The term "companion animal" means a dog or a cat. As used herein, the term "dog" and "canine" can be used interchangeably. In one embodiment, the companion animal can be a canine.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%. "Kibbles" means pieces of dry or semi-moist pet food which can have a pellet shape or any other shape. Non-limiting examples of kibbles include particulates; pellets; pieces of pet food, dehydrated meat, meat analog, vegetables, and combinations thereof; and pet snacks, such as meat or vegetable jerky, rawhide, and biscuits.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Moreover, the description of some steps as "optional" does not imply that the other steps which are not explicitly described as optional are necessarily required.

Any embodiment disclosed herein can be combined with any other embodiment disclosed herein.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

The relative terms "improved," "increased," "enhanced" and the like refer to the effects of the composition disclosed herein (a ketogenic composition or a therapeutically effective amount of a nutrient blend or component thereof) relative to a composition having a lower amount or lacking the ketogenic composition or nutrient blend or component thereof, but otherwise identical.

A "medium chain triglyceride" or "MCT" is a lipid in which three fatty acids are bound by ester linkages to a glycerol backbone, and at least two and preferably all three of the fatty acids are each between six and twelve carbons in length. The medium-chain fatty acids are caproic acid (comprising six carbon atoms or C6:0), caprylic acid (comprising eight carbon atoms or C8:0), capric acid (comprising ten carbon atoms or C10:0) and lauric acid (comprising twelve carbon atoms or C12:0). In one embodiment, the medium-chain fatty acids are mainly (e.g., at least 98%) in the form of triglycerides. A composition comprising "lipids consisting essentially of medium chain triglycerides" contains medium chain triglycerides as at least 20% of the lipids, in some embodiments at least 30% of the lipids, in other embodiments at least 40% of the lipids, and in some embodiments at least 50% of the lipids in the composition.

The term "ketogenic diet" means a diet having specific ratios of fat, carbohydrate, and protein such that an animal metabolizes fat into ketone bodies as the predominate source of energy in the animal. As such, in one embodiment, a ketogenic diet can be a diet having at least 40% fat. In one aspect, the diet can include less than 10% carbohydrates. In another embodiment, a ketogenic diet can include medium chain triglycerides.

As used herein "walnut" refers to any walnut species, including without limitation English walnut and black walnut, and include any portion or processing thereof including without limitation whole nut, ground walnut, walnut meal, and the like.

As used herein "maitake mushroom extract" refers to the mushroom *Grifola frondosa* and includes any portion thereof or any extract thereof.

Embodiments

In one embodiment, a method of minimizing fat accumulation in a growing animal without limiting caloric intake or preventing or treating obesity in an animal can comprise orally administering a ketogenic diet and a nutrient blend to the animal. Generally, the nutrient blend includes at least four nutrients selected from the group consisting of walnut, maitake mushroom extract, EGCG, turmeric root powder, lycopene, taurine, EPA, and DHA to the animal.

Generally, the methods include a ketogenic diet and the nutrient blend such that the animal or growing animal can avoid excessive fat accumulation or obesity. Such nutrients generally include walnut, maitake mushroom extract, EGCG, turmeric root powder, lycopene, taurine, EPA, and DHA. In various aspects, the composition can comprise at least 4 nutrients, 5 nutrients, 6 nutrients, 7 nutrients, or in one specific aspect, all 8 nutrients. In one aspect, the composition can include at least 4 nutrients including maitake mushroom extract, turmeric root powder, taurine, and walnut.

As discussed herein, the nutrients can be present in a therapeutically effective amount to provide a health benefit to an animal. Such nutrients can be present in various concentrations depending on the composition. In one embodiment, the composition can be a food. In such an embodiment, the nutrients can be present as follows: the walnut can be present in an amount of 5% to 20%, in one aspect, the walnut can be present in an amount of 10% to 15%; the maitake mushroom extract can be present in an amount of 0.0001% to 0.05%, in one aspect, the maitake mushroom extract can be present in an amount of 0.0001% to 0.025%; EGCG can be present in an amount of 0.01% to 0.5%, in one aspect, EGCG can be present in an amount of 0.05% to 0.1%; the turmeric root powder can be present in an amount of 1% to 8%; in one aspect, the turmeric root powder can be present in an amount of 3% to 5%; lycopene can be present in an amount of 0.001% to 0.01%; in one aspect, lycopene can be present in an amount of 0.005% to 0.008%; taurine can be present in an amount of 0.05% to 0.5%, in one aspect, taurine can be present in an amount of 0.1% to 0.3%; EPA can be present in an amount of 0.05% to 2%, in one aspect, EPA can be present in an amount of 0.1% to 1%; and DHA can be present in an amount of 0.05% to 2%, in one aspect, DHA can be present in an amount of 0.1% to 1%.

Additionally, in another embodiment, the composition can be a supplement. In such an embodiment, the nutrients can be present as follows: the walnut is present in an amount of 60.61% to 83.33% of the supplement, the maitake mushroom extract is present in an amount of 0.0017% to 0.076% of the supplement, the EGCG is present in an amount of 0.167% to 1.52% of the supplement of the supplement, the turmeric root powder is present in an amount of 16.67% to 24.24% of the supplement, the lycopene is present in an amount of 0.0167% to 0.033% of the supplement, the taurine is present in an amount of 0.833% to 1.52% of the supplement, the EPA is present in an amount of 0.833% to 6.06% of the supplement, and the DHA is present in an amount of 0.833% to 6.06% of the supplement.

Generally, the present nutrient blends can be used in conjunction with a ketogenic diet. As discussed, the nutrient blend can be part of a food or a supplement. In one aspect, the food can be a pet food. In another aspect, the food can be a complete and nutritionally balanced pet food. In another embodiment, the nutrient blend can be part of a treat, gravy, or other companion food item. The present nutrient blends can be used for imparting a health benefit to any animal. In one aspect, the animal can be a companion animal. In another aspect, the companion animal can be a dog. In another aspect, the companion animal can be a cat.

As discussed herein, the ketogenic diet can be any diet that provides or uses ketone bodies as the predominate energy source for the animal. In one embodiment, the ketogenic diet can be a diet that provides at least 40% fat and no more than 10% carbohydrates to an animal on a daily basis. In another embodiment, the ketogenic diet can be one that includes MCTs. In still another embodiment, the ketogenic diet can be one that provides ketone bodies to the animal.

In one embodiment, MCTs can be included in a diet or composition. In one aspect, the MCTs can be about 1 wt % to about 60 wt % of the composition or diet. In one aspect, the MCTs can be from about 1 wt % to about 20 wt % of the composition or diet. In other aspects, the MCTs can be from about 1 wt % to about 15 wt %, from about 1 wt % to about 10 wt %, or from about 2 wt % to about 10 wt % of the composition or diet. The MCTs may be prepared by any known process, such as direct esterification, rearrangement, fractionation and/or transesterification. For example, the medium chain triglycerides may be prepared from a source of vegetable oil, such as coconut oil, through a rearrangement process. The chain length and distribution thereof may vary depending on the source oil. For example, MCTs containing 1-10% C6, 30-60% C8, 30-60% C10 and 1-10% C12 can be derived from palm oil and/or coconut oil; in some embodiments, at least a portion of the MCTs are provided by coconut oil, but in other embodiments the composition does not contain coconut oil. MCTs containing at least about 95% C8 can be made by semi-synthetic esterification of octanoic acid to glycerin; in some embodiments thereof, the remainder of the fatty acids are C6 and C10. Mixtures comprising MCTs with about 50% total C8 and/or about 50% total C10 are also useful herein.

Generally, the present nutrient blends can be administered for sufficient time to impart a health benefit to an animal. In one embodiment, the administration can be on a regular basis. In one aspect, the regular basis can be on a daily basis. In some embodiments, the nutrient blends can be administered to the animal for a time period of at least one week, at least one month, at least two, three, four, five or six, seven, eight, nine, ten, eleven months; and in some embodiments, for at least one year, or even for the duration of the animal's life. During the time period, the nutrient blends can be administered to the animal at least one day per week, at least two days per week, at least three, four, five or six days per week; or even seven days per week. The nutrient blends can be administered in a single dose per day or in multiple separate doses per day.

In an embodiment, the nutrient blends can be administered in an amount that provides about 0.1 g to 10 g of walnut per kg body weight of the animal per day. In one aspect, 0.5 g to about 6.5 g of the walnut per kg body weight of the animal can be administered per day. In an embodiment, the nutrient blends can be administered in an amount that provides about 0.1 mg to 30 mg of maitake mushroom extract per kg body weight of the animal per day. In one aspect, 0.15 mg to about 20 mg of the maitake mushroom extract per kg body weight of the animal can be administered per day. In an embodiment, the nutrient blends can be administered in an amount that provides about 0.5 mg to 200 mg of EGCG per kg body weight of the animal per day. In one aspect, 1 mg to about 180 mg of the EGCG per kg body weight of the animal can be administered per day. In an embodiment, the nutrient blends can be administered in an amount that provides about 0.05 g to 5 g of turmeric root powder per kg body weight of the animal per day. In one aspect, 0.1 g to about 4 g of the turmeric root powder per kg body weight of the animal can be administered per day. In an embodiment, the nutrient blends can be administered in an amount that provides about 0.005 g to 1 g of lycopene per kg body weight of the animal per day. In one aspect, 0.01 g to about 0.5 g of the lycopene per kg body weight of the animal can be administered per day. In an embodiment, the nutrient blends can be administered in an amount that provides about 1 mg to 300 mg of taurine per kg body weight of the animal per day. In one aspect, 5 mg to about 200 mg of the taurine per kg body weight of the animal can be administered per day. In an embodiment, the nutrient blends can be administered in an amount that provides about 1 mg to 1000 mg of EPA per kg body weight of the animal per day. In one aspect, 5 mg to about 750 mg of the EPA per kg body weight of the animal can be administered per day. In an embodiment, the nutrient blends can be administered in an amount that provides about 1 mg to 1000 mg of DHA per kg body weight of the animal per day. In one aspect, 5 mg to about 750 mg of the DHA per kg body weight of the animal can be administered per day.

The pet food compositions disclosed herein can be any food formulated for consumption by a pet such as a dog. In an embodiment, the pet food composition provides complete nutrition as defined by the Association of American Feed Control Officials (AAFCO) and which depends on the type of animal for which the composition is intended (e.g., a dog).

The pet food composition can comprise meat, such as emulsified meat. Examples of suitable meat include poultry, beef, pork, lamb and fish, especially those types of meats suitable for pets. The meat can include any additional parts of an animal including offal. Some or all of the meat can be provided as one or more meat meals, namely meat that has been dried and ground to form substantially uniform-sized particles and as defined by AAFCO. Additionally or alternatively, vegetable protein can be used, such as pea protein, corn protein (e.g., ground corn or corn gluten), wheat protein (e.g., ground wheat or wheat gluten), soy protein (e.g., soybean meal, soy concentrate, or soy isolate), rice protein (e.g., ground rice or rice gluten) and the like.

The pet food compositions disclosed herein can comprise one or more of a vegetable oil, a flavorant, a colorant or water. Non-limiting examples of suitable vegetable oils include soybean oil, corn oil, cottonseed oil, sunflower oil, canola oil, peanut oil, safflower oil and the like. In some embodiments, the lipids in the composition can consist of the MCTs and one or more of any vegetable oil, any fish oil, the lipid from any meat, and any omega-3 fatty acids.

Non-limiting examples of suitable flavorants include yeast, tallow, rendered animal meals (e.g., poultry, beef, lamb, pork), flavor extracts or blends (e.g., grilled beef), animal digests, and the like. Non-limiting examples of suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as starches, humectants, oral care ingredients, preservatives, amino acids, fibers, prebiotics, sugars, animal oils, aromas, other oils additionally or alternatively to vegetable oil, salts, vitamins, minerals, probiotic microorganisms, bioactive molecules or combinations thereof.

Non-limiting examples of suitable starches include a grain such as corn, rice, wheat, barley, oats, potatoes, peas, beans, cassava, and the like, and mixtures of these grains, and can be included at least partially in any flour. Non-limiting examples of suitable humectants include salt, sugars, propylene glycol and polyhydric glycols such as glycerin and sorbitol, and the like. Non-limiting examples of suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

EXAMPLE

By way of example and not limitation, the following non-limiting study is illustrative of compositions and methods using nutrient blends and ketogenic compositions and diets, in one or more embodiments provided by the present disclosure.

Example 1—Weight Gain for Growing Animal

Female nude mice with 3-4 weeks age (n=40) were randomized into 4 groups based on the baseline body weight (n=10/group, n=5/cage). After one-week transition from original diet to experimental diets, each group was assigned to one of the four diets randomly. The initial body weight was recorded and was followed up weekly for 14 weeks. All the diets and food are freely accessed to the mice. Every week fresh diet was weighted and provided three times to mice. The consumption of food was calculated by subtracting the residual food.

The following four diets were used in the study. Control: AIN-93G (available from Research diets, Inc.) (18% protein, 7.2% fat, 63% carbohydrate, 5% fiber). Ketogenic diet (18% protein, 0% carbohydrate, 63% fat, 8.6% fiber). Ketogenic diet+nutrient blend (20.9% protein, 0% carbohydrate, 54.5% fat, 9.1% fiber). AIN-93G+nutrient blend (19.9% protein, 9.7% fat, 53.2% carbohydrate, 6.1% fiber). Nutrient blend (NB) composition: 11.3% whole walnut meal, 0.005% maitake mushroom extract, 0.05% EGCG, 3% turmeric root powder, 0.005% lycopene, 0.1% taurine, and 2% fish oil. Nutrient blend (NB) composition: 11.3% whole walnut meal, 0.005% maitake mushroom extract, 0.05% EGCG, 3% turmeric root powder, 0.005% lycopene, 0.1% taurine, and 2% fish oil.

The results of the 14 weeks of feeding show that only the ketogenic diet with the nutrient blend slowed down the body weight gain without limiting caloric intake (Table 1), indicating that the mice grew at normal rate without accumulating excessive body fat. Since excessive body fat accumulation in young animals are correlated with higher risk of obesity, the present blend can optimize growth and minimize the risk of obesity in growing animals and prevent obesity in adult animals.

TABLE 1

|  | AIN-93G | AIN-93G + Nutrient blend | Ketogenic diet | Ketogenic diet + Nutrient blend |
|---|---|---|---|---|
| Baseline bodyweight (g) | 16.2 | 16 | 15.8 | 16.2 |
| End of study Body weight (g) at 18 weeks of age | 27.9 | 26 | 27.6 | 25.1 |
| % increase | 72.2 | 62.5 | 74.7 | 54.9 |
| Average Caloric intake (calories per week/mouse) | 69.9 | 69.9 | 104.0 | 109.0 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:
1. A method of treating obesity in an animal in need thereof comprising orally administering to the animal in need thereof a nutrient blend comprising walnut, maitake mushroom extract, epigallocatechin gallate, turmeric root powder, lycopene, taurine, eicosapentaenoic acid, and docosahexaenoic acid; wherein the nutrient blend comprises:
  60.61 wt. % to 83.33 wt. % of the walnut,
  0.0017 wt. % to 0.076 wt. % of the maitake mushroom extract,
  0.167 wt. % to 1.52 wt. % of the epigallocatechin gallate,
  16.67 wt. % to 24.24 wt. % of the turmeric root powder,
  0.0167 wt. % to 0.033 wt. of the lycopene,
  0.833 wt. % to 1.52 wt. % of the taurine,
  0.833 wt. % to 6.06 wt. % of the eicosapentaenoic acid, and
  0.833 wt. % to 6.06 wt. % of the docosahexaenoic acid.
2. The method of claim 1, wherein the nutrient blend is a supplement.
3. The method of claim 1, further comprising adding the nutrient blend to a food.
4. The method of claim 3, wherein the food is a complete and nutritionally balanced pet food.
5. The method of claim 3, wherein the food comprises:
  5 wt. % to 20 wt. % of the walnut,
  0.0001 wt. % to 0.025 wt. % of the maitake mushroom extract,
  0.01 wt. % to 0.5 wt. % of the epigallocatechin gallate,
  1 wt. % to 8 wt. % of the turmeric root powder,
  0.001 wt. % to 0.01 wt. % of the lycopene,
  0.05 wt. % to 0.5 wt. % of the taurine,
  0.05 wt. % to 2 wt. % of the eicosapentaenoic acid, and
  0.05 wt. % to 2 wt. % of the docosahexaenoic acid.
6. The method of claim 1, wherein the animal is a companion animal.
7. The method of claim 1, wherein the animal is a dog.
8. The method of claim 1, further comprising administering the nutrient blend in conjunction with a ketogenic diet.
9. The method of claim 8, wherein t ketogenic diet includes administering a composition having 1% to 60% medium chain triglycerides.

10. The method of claim 8, wherein the Ketogenic diet includes administering ketone bodies to the animal.

11. The method of claim 8, wherein the ketogenic diet includes administering a diet having a fat content of at least 40% by weight.

12. The method of claim 8, wherein the Ketogenic diet includes administering a diet having a carbohydrate content of no more than 10% by weight.

13. The method of claim 1, wherein the administration is on a regular basis.

\* \* \* \* \*